US012805840B2

(12) United States Patent
Davies et al.

(10) Patent No.: US 12,805,840 B2
(45) Date of Patent: Nov. 24, 2026

(54) ULTRASOUND IMAGING DEVICE WITH THERMALLY CONDUCTIVE PLATE

(71) Applicant: PHILIPS IMAGE GUIDED THERAPY CORPORATION, San Diego, CA (US)

(72) Inventors: Stephen Charles Davies, El Dorado Hills, CA (US); Wojtek Sudol, Andover, MA (US); William John Ossmann, Acton, MA (US); Anjali Saini, Sudbury, MA (US); Mike Lavy, Stoneham, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/931,246

(22) Filed: Oct. 30, 2024

(65) Prior Publication Data

US 2025/0049417 A1 Feb. 13, 2025

Related U.S. Application Data

(63) Continuation of application No. 18/238,555, filed on Aug. 28, 2023, now Pat. No. 12,144,680, which is a
(Continued)

(51) Int. Cl.
*A61B 8/00* (2006.01)
*A61B 8/12* (2006.01)
(Continued)

(52) U.S. Cl.
CPC ................ *A61B 8/445* (2013.01); *A61B 8/12* (2013.01); *A61B 8/4488* (2013.01);
(Continued)

(58) Field of Classification Search
CPC ............ A61B 8/12; A61B 8/445; A61B 8/546
See application file for complete search history.

(56) References Cited

U.S. PATENT DOCUMENTS 4,521,476 A 6/1985 Asai et al.
2003/0028107 A1 2/2003 Miller et al.
(Continued)

FOREIGN PATENT DOCUMENTS

EP 3097861 A1 11/2016

OTHER PUBLICATIONS

International Search Report and Written Opinion of PCT/ EP2018/ 054805, dated Jun. 8, 2018.

*Primary Examiner* — Serkan Akar
*Assistant Examiner* — Tommy T Ly

(57) ABSTRACT

A device for imaging within a body of a patient is provided. In one embodiment, the device includes a flexible elongate member that can be inserted into the body of the patient. The device also has an imaging assembly that is disposed at and extending a length of a distal portion of the flexible elongate member. The imaging assembly may include an array of imaging elements that may have an outward surface and an inward surface. The imaging assembly may further include an integrated circuit adjacent to the inward surface of the array of imaging elements. The device may further include a conductive plate adjacent to and extending at least a portion of a length of the imaging assembly. The conductive plate may receive heat generated by at least one of the array of imaging elements or the integrated circuit.

20 Claims, 7 Drawing Sheets

Related U.S. Application Data continuation of application No. 16/489,857, filed as application No. PCT/EP2018/054805 on Feb. 27, 2018, now Pat. No. 11,737,728.

(60) Provisional application No. 62/468,046, filed on Mar. 7, 2017.

(51) Int. Cl.
*A61M 25/00* (2006.01)
*A61M 25/01* (2006.01)

(52) U.S. Cl.
CPC ............ *A61B 8/4494* (2013.01); *A61B 8/546* (2013.01); *A61M 25/0009* (2013.01); *A61M 25/0108* (2013.01)

(56) References Cited

U.S. PATENT DOCUMENTS

| | | | | |
|---|---|---|---|---|
| 2003/0028108 | A1* | 2/2003 | Miller | A61B 8/4483 600/437 |
| 2007/0031996 | A1 | 2/2007 | Chopin et al. | |
| 2008/0009745 | A1* | 1/2008 | Hossack | A61B 17/2202 600/463 |
| 2008/0161890 | A1 | 7/2008 | Lafontaine | |
| 2008/0300492 | A1* | 12/2008 | Nagano | A61B 8/546 600/462 |
| 2012/0108979 | A1* | 5/2012 | Franklin | A61B 8/445 600/463 |
| 2013/0261455 | A1 | 10/2013 | Thaphiyal et al. | |
| 2015/0115773 | A1* | 4/2015 | Li | A61B 8/12 29/25.35 |
| 2015/0150571 | A1 | 6/2015 | Nita et al. | |
| 2015/0276685 | A1* | 10/2015 | Yasuhara | G01N 29/24 73/632 |
| 2015/0289854 | A1* | 10/2015 | Cho | H05K 1/0204 600/463 |
| 2016/0066881 | A1* | 3/2016 | Li | A61B 8/12 600/443 |
| 2016/0126445 | A1* | 5/2016 | Kiyose | A61B 8/4427 310/334 |
| 2016/0278737 | A1 | 9/2016 | Fujimura | |
| 2017/0007213 | A1* | 1/2017 | Motoki | B06B 1/0622 |
| 2017/0188995 | A1 | 7/2017 | Bruestle et al. | |

* cited by examiner

ULTRASOUND IMAGING DEVICE WITH THERMALLY CONDUCTIVE PLATE

CROSS-REFERENCE TO PRIOR APPLICATIONS

This application is a continuation of U.S. application Ser. No. 18/238,555, filed on Aug. 28, 2023, which is a U.S. Continuation of Ser. No. 16/489,857, filed on Aug. 29, 2019, now U.S. Pat. No. 11,737,728, which is the U.S. National Phase application under 35 U.S.C. § 371 of International Application No. PCT/EP2018/054805, filed on Feb. 27, 2018, which claims the benefit of U.S. Provisional Application No. 62/468,046, filed on Mar. 7, 2017. These applications are hereby incorporated by reference herein in their entirety.

TECHNICAL FIELD

The present disclosure relates generally to devices for imaging within a body of a subject.

BACKGROUND

Diagnostic and therapeutic ultrasound catheters (or guidewires) have been designed for imaging inside many areas of the human body. Ultrasound catheters may be used and adapted for a variety of applications, including intracardiac echocardiography (ICE), transesophageal echocardiogram, intervascular imaging, and imaging of other intraluminal or fluid-filled structures.

For example, ICE is emerging as the standard of care for imaging within the heart and surrounding structures, for example, to guide and facilitate transseptal lumen punctures, left atrial appendage closures, atrial fibrillation ablation, and valve repairs. An ICE catheter typically includes an array of transducers at the distal portion of the catheter and a plurality of signal wires connecting the array to an imaging console. The array may be flat, curved, annular or may have any other configuration. The same transducers or separate transducers may be used to generate and receive echoes from the tissue. The signal wires may carry signals to control the array and transmit echo signals to the imaging console. The assembly may provide rotational, 2-way, or 4-way steering mechanisms such that anterior, posterior, left, and/or right views of the heart anatomy may be imaged.

A problem common to most ultrasound catheters, including ICE catheters, is heat generated during imaging. During imaging, transducers convert electrical energy into mechanical energy and vice versa. Conversion of energy from one form to another via a transducer is rarely 100% efficient. The inefficiencies often manifest themselves in other forms of energy, such as heat. If the heat is not managed, undesirable blood coagulation, thrombogenesis, tissue damage and denaturing can occur at relatively modest temperature rises above body temperature. Currently, the heat generated by catheters is managed by limiting the acoustic power generated by the transducers. While desirably reducing heat, limiting the acoustic power also has the undesirable side effects of reducing overall signal strength, both transmitted and received, thereby causing lower image quality. Thus, limits on acoustic output can infringe on a doctor's ability to easily obtain clinically relevant images.

SUMMARY

The present disclosure relates to imaging assemblies at a distal portion of an imaging device. A thermally conductive plate is disposed at the distal portion. The plate can be metal in some embodiments. The plate functions to draw heat away from an ultrasound imaging array and various electronic components disposed at the distal portion of the imaging device. This allows for the imaging device to operate at higher power and/or for longer periods of time, which allow for better quality images of tissue within the body. For example, the imaging assembly can include the imaging array formed on an integrated circuit and an interconnect board. The integrated circuit and interconnect board can be coupled to a thermally conductive acoustic backing material, which is mechanically attached to the thermally conductive plate. The plate also strengthens the distal portion of the imaging device and inhibits bending/deflection that could damage the imaging array.

Embodiments of the present disclosure provide a device for imaging within a body of a patient that include a flexible elongate member that may be inserted into the body of the patient. The device may also include an imaging assembly disposed at and extending a length of a distal portion of the flexible elongate member. The imaging assembly may include an array of imaging elements that may have an outward surface and an inward surface. The imaging assembly may further include an integrated circuit adjacent to the inward surface of the array of imaging elements. The device may further include a conductive plate adjacent to and extending at least a portion of a length of the imaging assembly. The conductive plate may receive heat generated by at least one of the array of imaging elements or the integrated circuit.

In some embodiments, the plate may have a stiffness greater than a stiffness of the array of imaging elements such that the plate may inhibit deflection of the array of imaging elements. In some examples, the plate can include one or more metals. In some examples, the plate can be radiopaque. In some embodiments, the imaging assembly may include an acoustic backing material that may have a first surface and a second surface opposite the first surface. In some examples, the second surface of the first electronic component may be coupled to the first surface of the acoustic backing material. In some other examples, the second surface of the acoustic backing material may be coupled to the plate. In some embodiments, the acoustic backing material is thermally conductive such that the heat generated by at least one of the array of imaging elements or the electronic circuit is received by the plate via the acoustic backing material.

In some embodiments, a cross section the plate may have a rectangular shape, a t-shape, or a semi-circular shape. In some examples, an outward surface of the array of imaging elements may face a plane within the body of the patient being imaged. In some embodiments, the integrated circuit may have a first surface and a second surface opposite the first surface such that the first surface of the integrated circuit may be coupled to the array of imaging elements.

In some embodiments, an electronic component may be in communication with at least one of the array of imaging elements or the integrated circuit such that the plate may also receive heat generated by the electronic component. In some examples, the electronic component may be in contact with the acoustic backing material of the imaging assembly. In some examples, the electronic component is an interconnect board. In some examples, the integrated circuit may control the array of imaging elements.

In some embodiments, a method of manufacturing an imaging device includes providing a conductive plate and providing an imaging assembly. The imaging assembly may define a length and may have an array of imaging elements. The array of imaging elements may have an inward surface and an outward surface. The imaging assembly may further include an integrated circuit that may be adjacent to the inward surface and may be in communication with the array of imaging elements. The method also includes establishing thermal contact between the plate and at least one of the integrated circuit or the array of imaging elements. The plate may be adjacent to and may extend at least a portion of the length of the imaging assembly. The method further includes disposing the plate and imaging assembly within a distal portion of a flexible elongate member.

In some embodiments, the method of manufacturing the imaging device may further include obtaining the thermally conductive plate and obtaining a plate assembly comprising a metal and a foil. The method may further include etching a plurality of plates in the metal, but not the foil, of the plate assembly. In some examples, the method may include obtaining a plurality of imaging assemblies and coupling the surface of the acoustic backing material of each of the plurality of imaging assemblies to a respective plate of the plurality of plates to form a plurality of subassemblies. The method may also include establishing thermal contact between the plate and an interconnect board. The method may also include singulating the subassemblies such that singulating may include etching the foil of the plate assembly.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
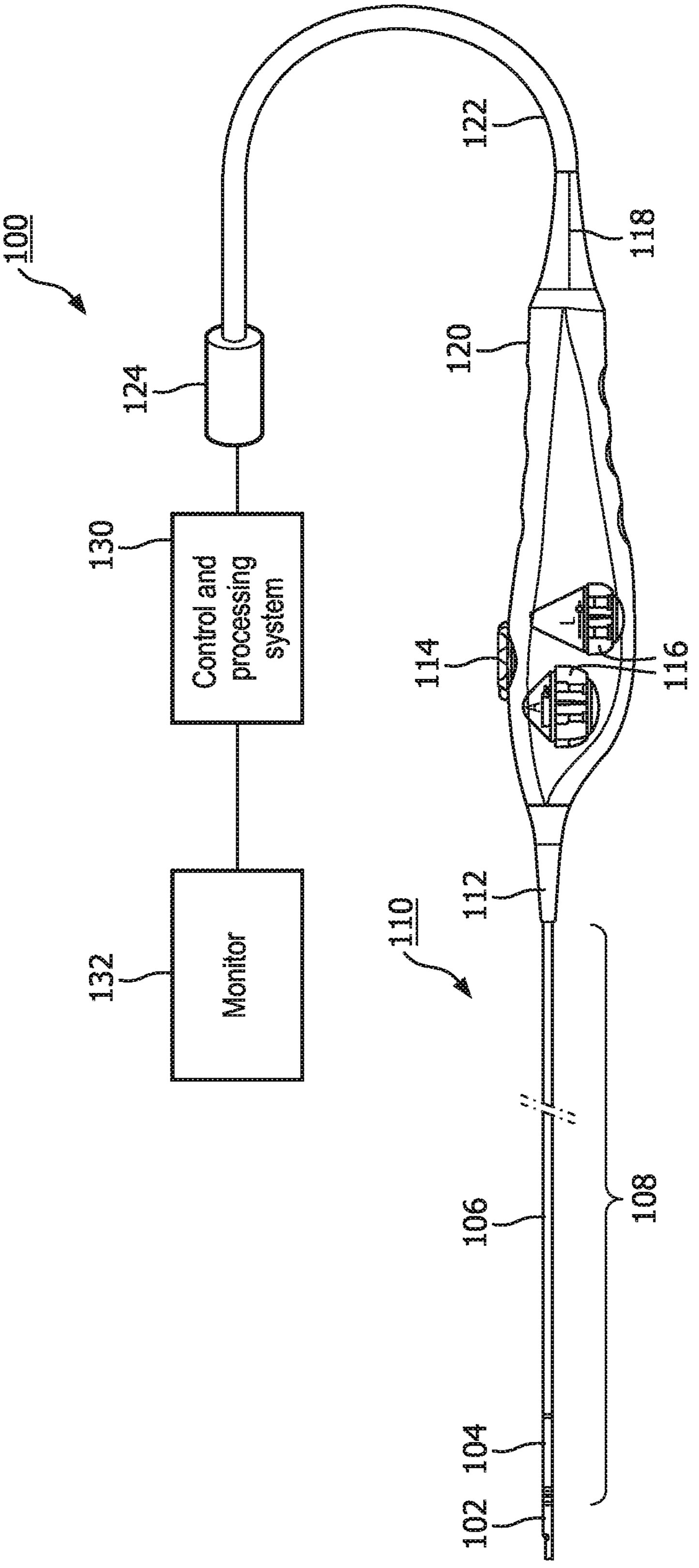
FIG. 1 is a schematic diagram of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system may be described in terms of imaging fluid filled structures, it is understood that it is not intended to be limited to this application and for example it can be used for imaging within a body of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Embodiments of the present disclosure implement a thermally conductive member, e.g., a plate, at the distal portion of an imaging device. The plate serves as a heat sink that more evenly distributes heat generated by the ultrasound imaging array and/or electronic components, e.g., integrated circuits or interconnect boards, in communication with the ultrasound imaging array. The plate also strengthens of the imaging device such that the distal portion does not bend and damage/destroy the imaging array.

The embodiments described herein provide numerous advantages. Complicated surgeries are more frequently accomplished using minimally invasive procedures. A key in minimally invasive procedures is the ability to provide quality images within the body to assess, monitor, or guide the intervention. For example, the ability to image within the vasculature and the heart with essentially the same resolution as externally. As the design and construction of invasive ultrasound transducers becomes more sophisticated so their power consumption and resultant thermal dissipation goes up. This invention disclosure describes a way to redistribute the thermal energy generated in the transducer and control circuitry so as to reduce the highest surface temperature of the device thus making it feasible to run at high powers or for longer durations. In fact, a better image quality can be attained from ultrasound probes that can operate at higher acoustic output powers.

FIG. 1 is a schematic diagram of an imaging system 100, according to embodiments of the present disclosure. The system 100 that can be used for imaging within a body of a patient may include an imaging device 110, a connector 124, a control and processing system 130, such as a console and/or a computer, and a monitor 132. The imaging device 110 includes an imaging assembly 102 at the tip of a flexible elongate member 108, and a handle 120. The imaging assembly 102 can include one or more ultrasound transducer elements, such as an array of transducer elements, and associated electronic circuitry. In some embodiments, the imaging system 100 is used for generating 2D and/or 3D images. For example, the imaging assembly can include a 1D imaging array for 2D imaging or a 2D imaging array for 3D imaging. In some examples, the imaging system 100 is used for generating x-plane images at two different viewing directions perpendicular to each other. The transducer elements and/or electronic circuitry can be referenced as an imaging core or imaging assembly in various embodiments.

The flexible elongate member 108 includes a distal portion 104 and a proximal portion 106. The imaging assembly 102 can be directly or indirectly coupled to the distal portion 104 of the flexible elongate member 108. For example, the imaging assembly 102 can be positioned within a tip member (e.g., tip member 200 of FIG. 2) and the tip member can be coupled to the distal portion 104 of the flexible elongate member 108. The imaging assembly 102 can extend a length of the flexible elongate member 108, such as the length of the distal portion 104. The proximal end of the proximal portion 106 is attached to the handle 120, for example, by a resilient strain reliever 112, for manipulation of the imaging device 110 and manual control of the imaging device 110. The handle 120 can include actuators 116, a clutch 114, and/or other steering control components for steering the imaging device 110 in one or more directions, such as by deflecting the imaging assembly 102 and the distal portion 104.

The handle 120 is connected to the connector 124 via another strain reliever 118 and a connection cable 122. The connector 124 may be configured in any suitable configurations to interconnect with the control and processing system 130 and the monitor 132 for processing, storing, analyzing, manipulating, and displaying data obtained from signals generated by the imaging core at the imaging assembly 102. The control and processing system 130 can include one or more processors, memory, one or more input devices, such as keyboards and any suitable command control interface device. The control and processing system 130 can be operable to facilitate the features of the imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the imaging assembly 102 and the distal portion 104 in a left-right plane and the other actuator 116 may deflect the imaging assembly 102 and the distal portion 104 in an anterior-posterior plane. The clutch 114 provides a locking mechanism to lock the positions of the actuators 116 and in turn the deflection of the flexible elongate member while imaging the area of interest.

The imaging process may include activating the ultrasound transducer elements on the imaging assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the control and processing system 130 where the ultrasound image is reconstructed and displayed on the monitor 132. In some embodiments, the processing system 130 can control the activation of the ultrasound transducer elements and the reception of the echo signals. In some embodiments, the control and processing system 130 and the monitor 132 may be part of the same system.

The system 100 may be utilized in a variety of applications such as transseptal lumen punctures, left atrial appendage closures, atrial fibrillation ablation, and valve repairs. Generally, the system 100 can be used to image vessels, structures, lumens, and/or any suitable anatomy/tissue within a body of a patient including any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the imaging device 110 may be used to examine man-made structures such as, but without limitation, heart valves, stents, shunts, filters and other devices. For example, the device 110 can be positioned within fluid filled or surrounded structures, both natural and man-made, such as within a body of a patient. The vessels, structures, lumens, and anatomy/tissue can include a blood vessel, as an artery or a vein of a patient's vascular system, including cardiac vasculature, peripheral vasculature, neural vasculature, renal vasculature, and/or any suitable lumen inside the body.

The system 100 is suitable for use with any catheterization procedure. In addition, the imaging assembly 102 may include any suitable physiological sensor or component for diagnostic, treatment, and/or therapy. For example, the imaging assembly can include an imaging component, an ablation component, a cutting component, a morcellation component, a pressure-sensing component, a flow-sensing component, a temperature-sensing component, and/or combinations thereof. In some examples, the system 100 may be described in the context of intraluminal imaging procedures.

Figure 2:
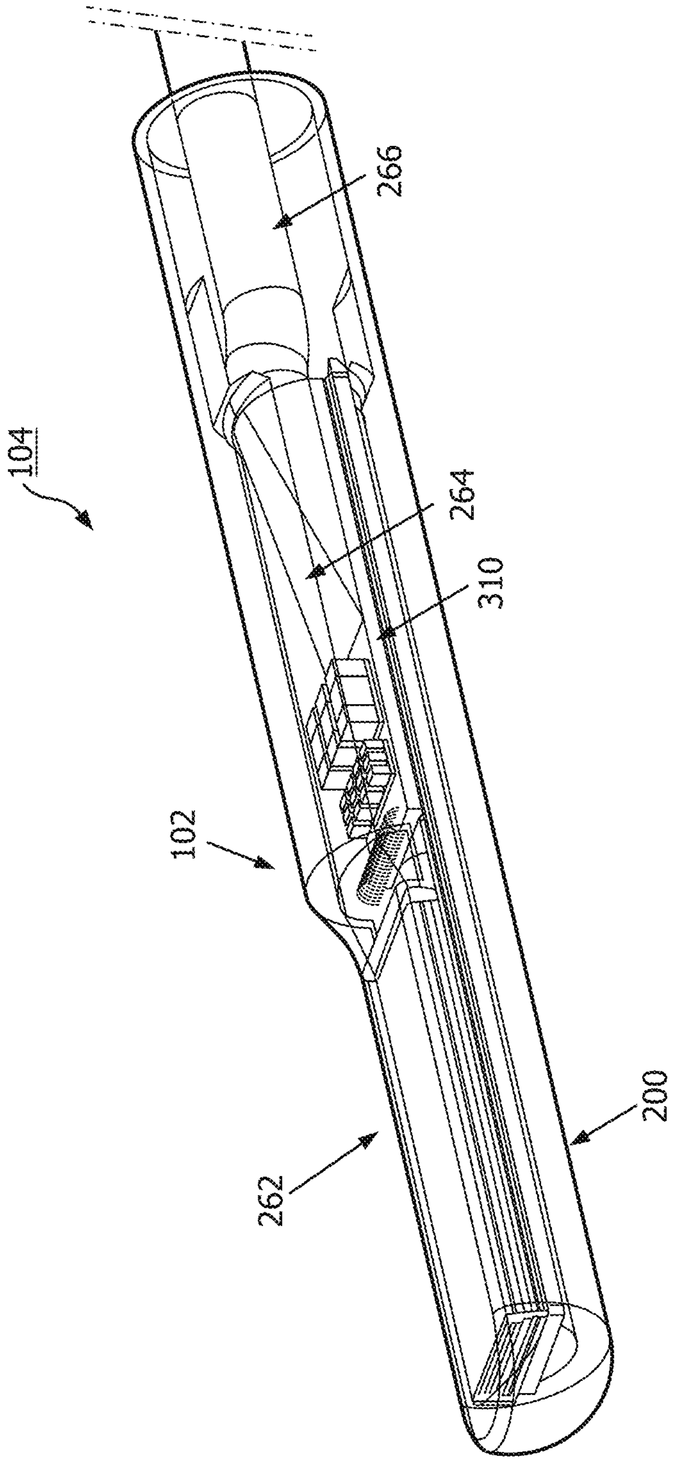
FIG. 2 is a perspective view of a distal portion of the imaging device, according to aspects of the present disclosure.

FIG. 2 is a perspective view of the distal portion 104 of the imaging device 110, including the imaging assembly 102, according to embodiments of the present disclosure. The imaging assembly 102 is illustrated with the imaging core 262, including an array of transducer elements and associated circuitry, disposed within a tip member 200. The tip member 200 may be a housing for the imaging assembly 102 and include an acoustic window through which ultrasound energy and reflected echoes propagate. The imaging assembly 102 can be disposed within the tip member 200, and the tip member 200 can be coupled to the distal portion 104 of the flexible elongate member 108. The material type and the wall thickness of the tip member 200 are selected to minimize acoustic distortion, attenuation, and/or reflection. The tip member 200 can also include other features, for example, a guidewire lumen, holes, or other geometry to accommodate additional devices or features such as pressure sensors, drug delivery mechanisms, and/or any suitable interventional features. The tip member 200 may be an optically and/or acoustically translucent cover for the imaging assembly 102. The imaging assembly 102 includes the interconnect board 310 in electrical communication with the imaging core 262. The imaging core 262 is coupled to the electrical cable 266 via the electrical interconnection 264 to the interconnect board 310. The electrical cable 266 can extend from the distal portion 104 proximally through the flexible elongate member 108 and the device 110 to the connector 124, as shown in FIG. 1. In some embodiments, the diameter of the distal portion of the imaging device may be approximately 3 mm.

Figure 3A:
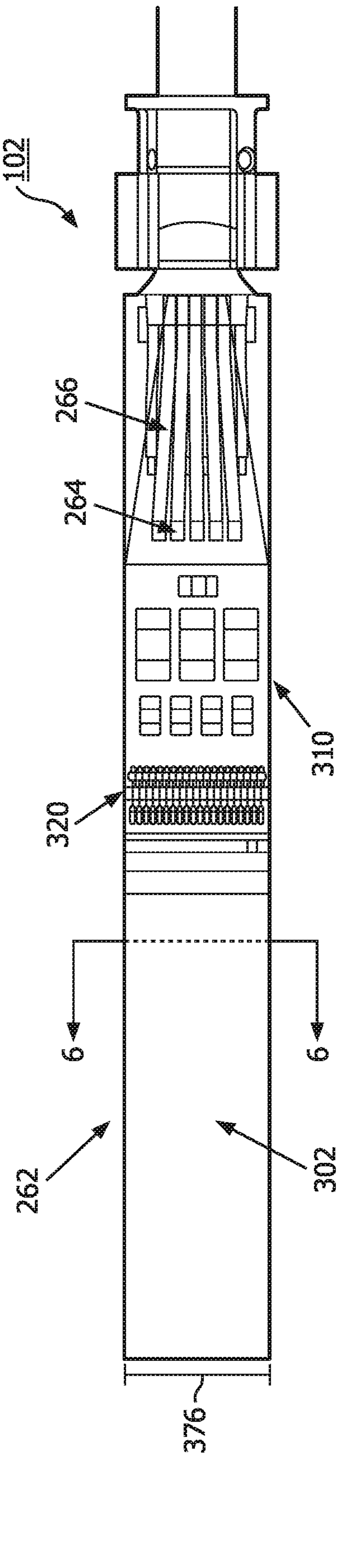
FIG. 3A is a top view of an imaging assembly, according to aspects of the present disclosure.
Figure 3B:
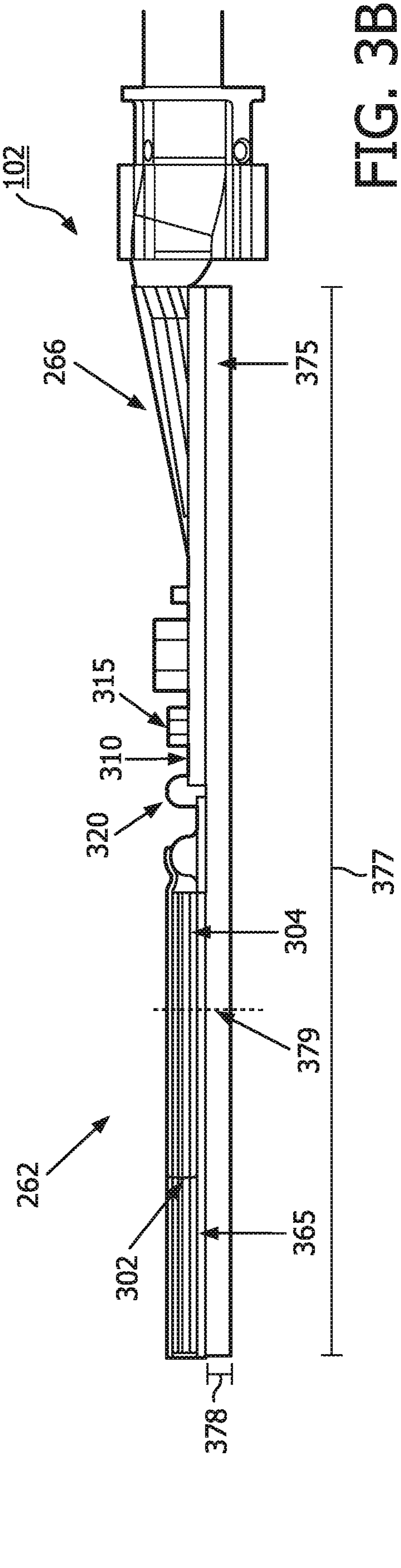
FIG. 3B is a side view of the imaging assembly, according to aspects of the present disclosure.
Figure 4:
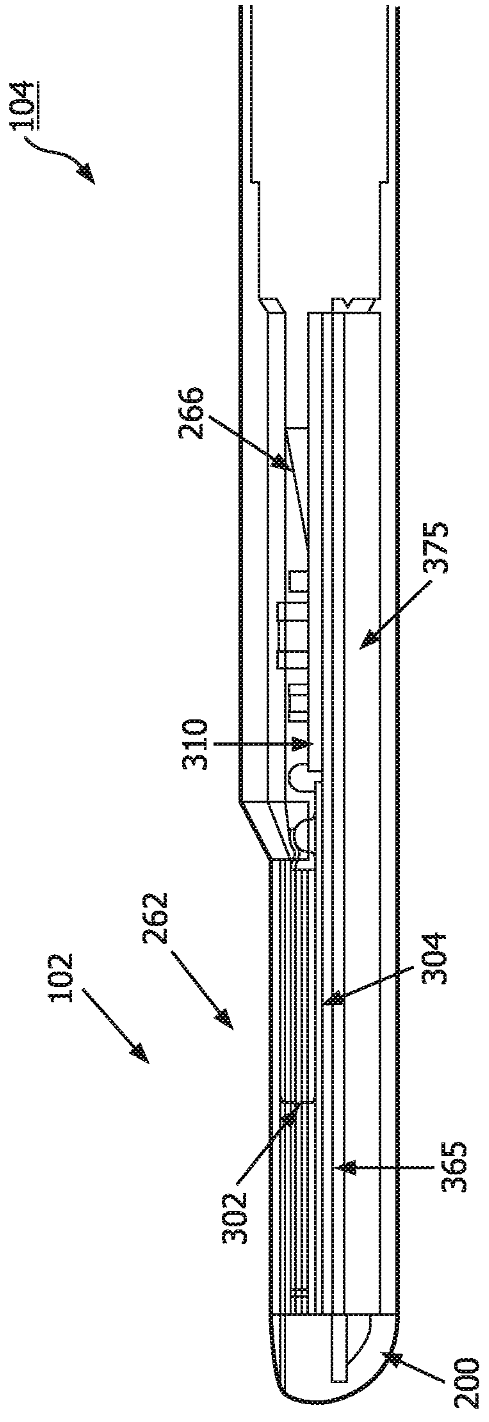
FIG. 4 is a side view of a distal portion of an imaging device, according to aspects of the present disclosure.

FIG. 3A is a top view and FIG. 3B is a side view of an imaging assembly 102, according to embodiments of the present disclosure. FIG. 4 is a side view of the distal portion 104 of the imaging device 110, including the imaging assembly 102 positioned within the tip member 200.

The imaging assembly 102 is illustrated with the imaging core 262 including an array of imaging elements 302. For example, acoustic imaging elements 302 may be of any suitable type, including lead zirconate titanate (PZT), piezoelectric or capacitive micromachined ultrasonic transducer (PMUT or CMUT). In some embodiments, the array 302 includes plurality of layers, such as a PZT layer, one or more electrode layers, one or more matching layers, etc. In some examples, the array of imaging elements 302 can be in the form of an array of more than 800 imaging elements. In this regard, the imaging elements 302 may be arranged in a 2-dimensional array having a same length and a same width such that the array of imaging elements 302 may have a symmetrical aperture. In some examples, the imaging elements 302 may be arranged in a 2-dimensional array having a length greater than a width such that more imaging elements 302 extend along the length of the array than across the width. As a result, the array of imaging elements 302 may have an asymmetrical aperture.

As shown in FIGS. 3A, 3B, and 4, the imaging assembly 102 can also include electronic components 304, 310 in electrical communication with the imaging elements 302, each other, and/or the electrical cable 266. In some embodiments, the integrated circuit 304 and/310 can be rigid or flexible printed circuit assemblies. For example, the integrated circuit 304 can be an integrated circuit, such as an application specific integrated circuit (ASIC), configured to control operation of the imaging elements 302. For example, the integrated circuit 304 can drive the transducer elements 302, provide switching between signal lines, generation of the excitation pulse, and/or other features associated with intraluminal imaging, imaging fluid filled structures, or imaging within a body of a patient. In some examples, the integrated circuit 304 may be a micro-beamformer integrated circuit (IC) that can control the array of imaging elements 302 and can perform beam forming for the array imaging elements 302. In some embodiments, the transducer elements 302 are formed on, e.g., a substrate of the integrated circuit 304. In some embodiments, the array of ultrasound imaging transducers 302 are directly flip-chip mounted to the integrated circuit 304. Piezoelectric elements 302 typically would be attached to the IC by flip-chip mounting an assembly of acoustic layers and sawing into individual elements. MUT elements may be flip-chip mounted as a unit or grown directly on top of the integrated circuit 304. In some examples, mass termination of the acoustic imaging elements 302 is done at the integrated circuit 304. In some embodiments, the integrated circuit 304 lies directly underneath the array of acoustic elements 302 and is electrically connected to them. The integrated circuit 304 may be in physical and thermal contact with the imaging elements 302.

The electronic component 310 of the imaging assembly 102 can be an interconnect board and/or interposer. In some examples, the interconnect board 310 is electrically and/or mechanically connected to the integrated circuit 304 through any suitable means such as wire bonding 320, as in illustrated in FIGS. 3A and 3B. In some examples, as shown in FIG. 3B, the interconnect board 310 may include one or more sensors 315 for measuring a temperature of the imaging assembly.

The electrical cable 266 is in communication with the imaging elements 302, the integrated circuit 304, and/or the interconnect board 310. The electrical cable 266 includes one or more power lines for feeding power to the integrated circuit 304, one or more control lines for communicating control signals to the integrated circuit 304, and one or more signal lines for transferring imaging signals. In some examples, wires of the electrical cable 266 are in electrical communication with the integrated circuit 304 is in through the interconnect board 310. The cable 266 can be coupled to the electrical interconnection 264 on the interconnect board 310. In some examples, the imaging assembly 102 is configured such that the electrical cable 266 is directly coupled to the integrated circuit 304.

The imaging assembly 102 includes an acoustic backing material 365, as shown in FIGS. 3B and 4. The acoustic backing material 365 can be configured to attenuate ultrasound signals emitted by the imaging elements 302 in an undesired direction. In some examples, the acoustic backing material 365 can be a dampening material for ultrasound waves and prevent back propagation of the ultrasound waves. Accordingly, the acoustic backing material 365 facilitates transmission of the ultrasound signals by the imaging elements 302 in the desired direction, such as through the acoustic window of the tip member 200. In some examples, the acoustic backing material 365 is thermally conductive.

According to aspects of the present disclosure, the distal portion 104 of the device 110 and/or the imaging assembly 102 includes a plate 375. The plate 375 can take the form of a square or rectangular bar or bars. The plate 375 can be shaped as a rectangular prism in some instances. In some embodiments, the plate 375 can comprise a single metal rod or a plurality of rods parallel and adjacent to each other. The plate 375 may comprise any suitable material, such a ceramic, diamond, tungsten carbide, metal, such as aluminium, copper, or titanium, or a metal alloy, such as steel or beryllium copper. In some embodiments, the plate 375 can be radiopaque. In that regard, metals are electron dense and therefore highly radiopaque. This advantageously allows for the distal portion 104 of the device 110 to be more easily identified in radiographic images, such as x-ray, angiography, or fluoroscopy.

In some embodiments, the plate 375 is conductive. The plate 375 can be referenced as a heat sink in some instances. The plate 375 may be thermally conductive. In some embodiments, the plate 375 may be electrically conductive. For example, the plate 375 receives heat generated by the array of imaging elements 302, the integrated circuit 304, and/or the interconnect board 310 as a by productive of the operation of the imaging device 110. In that regard, the plate 375 is in thermal contact with the array of imaging elements 302, the integrated circuit 304, and/or the interconnect board 310. Without the plate 375, the heat is concentrated at the location of the array of imaging elements 302, the integrated circuit 304, and/or the interconnect board 310. Thus, any temperature increase at the distal portion 104 of the imaging device 110 is localized. The plate 375 provides a path by which heat energy could travel from the point of highest temperature to the point of lowest temperature. This advantageously distributes the heat within the imaging device 110 and avoids any specific location of the distal portion 104 from a disproportionately large temperature increase. Additionally, by distributing the heating using the plate 375, a greater surface area of blood is in contact with the warmer portions of the imaging device 110, which allows for the blood to more easily dissipate the heat without damaging the blood. The greater the thermal conductivity of the material used for the plate 375, the more efficiently heat will be removed from the transducer and integrated circuit area.

The plate 375 is also in thermal contact with the acoustic backing material 365. As mentioned above, the acoustic backing material 365 can be thermally conductive. In such embodiments, the acoustic backing material 365 and the plate 375 serve as a two stage heat sink for the imaging device 110. In that regard, heat generated by the array of imaging elements 302, the integrated circuit 304, and/or the interconnect board 310 is first distributed as it is received by the acoustic backing material 365, and the distributed for a second time as it is received by the plate 375.

In some examples, the plate 375 may exhibit a stiffness greater than a stiffness of the array of imaging elements 302 such that the plate 375 inhibits deflection of the array of imaging elements 302. The plate 375 also advantageously provides structural support for the imaging assembly 102 by increasing the tensile/compressive strength and/or rigidity of the distal portion 104 of the imaging device 110. In that regard, the tensile/compressive strength and/or rigidity of the material of the plate 375 may be greater than the rigidity of the array 302, the integrated circuit 304, the interconnect board 310, and/or the materials of the tip member 200. By implementing the plate 375 within the imaging device 110, the distal portion 104 is less likely to experience bending or deflection that damages or destroys the array 302. In some embodiments, the plate 375 is not thermally conductive and is implemented in the imaging device 110 only to provide structural support. In other embodiments, the plate 375 is both thermally conductive and provides structural support for the imaging assembly 102.

As shown in FIGS. 3B and 4, the plate 375 is positioned within the distal portion 104 in longitudinal and lateral alignment with the imaging assembly 102. For example, the plate 375 can extend adjacent to and extend at least a portion of the length of the imaging assembly 102. In that regard, the dimensions 376, 377, 378 of the plate 375 can be selected to span all or at least a portion of the length and all or at least a portion of the width of the array of imaging elements 302, the integrated circuit 304, and/or the interconnect board 310. In certain embodiments, the plate 375 may extend beyond the length or width of those elements. In some embodiments, the width 376 of the plate 375 can be between approximately 2 mm and 4 mm, including values such as 3 mm. The length 377 of the plate 375 can be between approximately 5 mm and 25 mm, in some embodiments. The height 378 of the plate 375 can be between 0.1 mm and 1 mm in some embodiments. In some embodiments, the surface area of the plate 375 can be maximized to increase the radiating surface area and therefore the rate of energy transfer. In some examples, the width 376, height 378, and length 377, of the plate 375 may be chosen based on an amount of heat dissipation desired. In some embodiments, the distal edge of the array of imaging elements 302 and integrated circuit 304 can be aligned with the distal edge of the plate 375. In some embodiments, the plate 375 may extend in a proximal direction beyond the proximal edge of the array of imaging elements 302 and integrated circuit 304. The proximal edge of the interconnect board 310 may be aligned with the proximal edge of the plate 375. The acoustic backing material 365 may be laterally and longitudinally aligned with the plate 375. In some embodiments, one or more edges (sides) of the plate 375 may be aligned with one or more edges (sides) of the array of imaging elements 302 and/or the integrated circuit 304. For example, the imaging assembly 102 includes one or more components in a stacked configuration, including the plate 375, array 302, integrated circuit 304, backing material 365, interconnect board 310, etc. One or more edges (sides) of the plate 375 may be flush with the edges (sides) of one or more of the other stacked components of the imaging assembly 102.

One or more of the array 302, the integrated circuit 304, the interconnect board 310, the acoustic backing material 365, and/or the plate 375 can be mechanically and/or thermally coupled using any suitable adhesive such as glue or epoxy. In some embodiments, as shown in the orientation of the imaging assembly 102 in FIGS. 3B and 4, the array 302 is formed on a superior surface of the integrated circuit 304. For example, the array 302 can include an outward/superior surface and an inward/inferior surface. The superior/outward surface of the array 302 can be positioned to face the imaging plane of anatomy within the patient body that is being imaged. The integrated circuit 304 can be adjacent to the inferior/inward surface of the array 302. An inferior surface of the integrated circuit 304, opposite the superior surface, can be in contact with and coupled to a superior surface of the acoustic backing layer 365. An inferior surface of the interconnect board 310, opposite a superior surface, can be in contact with and coupled to the superior surface of the acoustic backing layer 365. The inferior surface of the acoustic backing layer 365, opposite the superior surface, can be in contact with and coupled to a superior surface of the plate 375. An inferior surface of the plate 375, opposite the superior surface, can be adjacent to the tip member 200.

Figure 5:
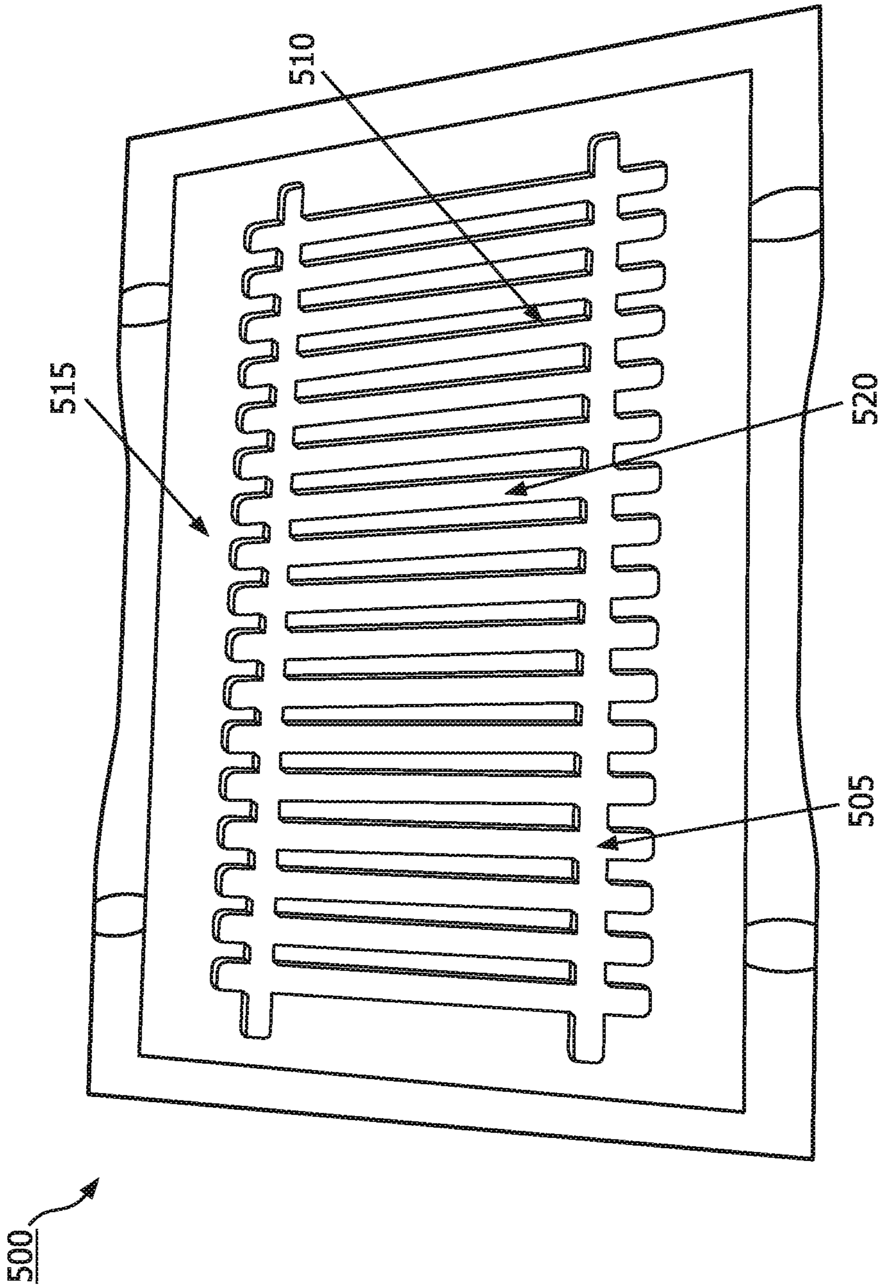
FIG. 5 is a top view of a plate assembly including a plurality of conductive plates, according to aspects of the present disclosure.

FIG. 5 is a top view of a plate assembly 500 including a plurality of thermally conductive plates 510, according to aspects of the present disclosure. FIG. 5 may illustrate a stage during the method of manufacturing the imaging device 110. Any suitable number of plates 510 can be formed during a batch process, such as one, ten, sixteen, or more plates. The plate assembly 500 can include a block 515 coupled to a foil 505, such as with any suitable adhesive. The block 515 and/or the foil 505 can be a metal or metal alloy in some embodiment. In some embodiments, the block 515 can be beryllium copper and the foil 505 can be aluminum or steel. Manufacturing the plate assembly 500 may start with the block 515 as being a solid, complete rectangular prism. During a step of manufacturing, the block 515, but not the foil 505, is etched to form islands or plates 510. FIG. 5 illustrates the plate assembly 500 after this step. By etching only the block 515 and not the foil 505, the plates 510 are formed with the desired shape while maintaining the spacing between the plates 510. The strips 520 of foil 505, attached to individual plates 510, maintain the relative positioning between the plates 510. The etching can be very accurate and the precise spacing between the plates 510 is known. In later steps of manufacturing the imaging device 110, various components of the imaging assembly 102 can be precisely positioned on and coupled to the respective plates 510 while the plates 510 are still attached to the foil 505 using, e.g., pick and place processes. In some embodiments, the assembly 500 can include fiducial markers to facilitate precise cutting and/or positioning of components on the plates 510. In yet later steps of manufacturing, the plates 510 can be singulated by cutting/dicing through the foil such that the plates and any coupled imaging components can be moved relative to one another.

Manufacturing may be more efficient as a result of forming a plurality of plates 510 in a single step. In some embodiments, ICE devices are necessarily small as they have to travel to the chambers of the heart via blood vessels. As a consequence, it is necessary to assemble the tips with a high degree of accuracy such that the assembly fits within the confines of the tip. To achieve this a batch process could be considered whereby the metal bar is etched from a larger plate of metal and supported by a very thin metal foil. The etching process has a number of advantages over other methods of manufacture. Etching is a very accurate process, the processing technique leaves a chamfer on the bars with ease the fit of the assembled device in the tip and the process readily lends itself pairing with other manufacturing methods that are currently employed in the construction of the transducer assembly.

Figure 6A:
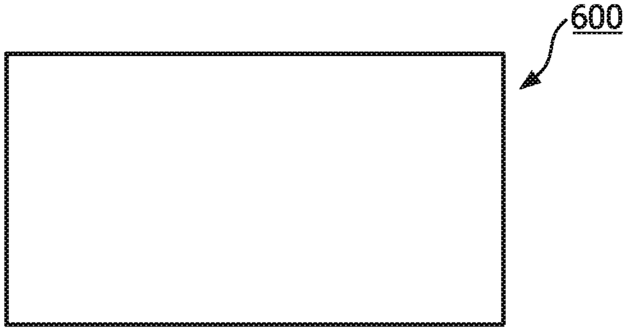
FIGS. 6A, 6B, and 6C are cross-sectional images of a conductive plate, according to aspects of the present disclosure.
Figure 6B:
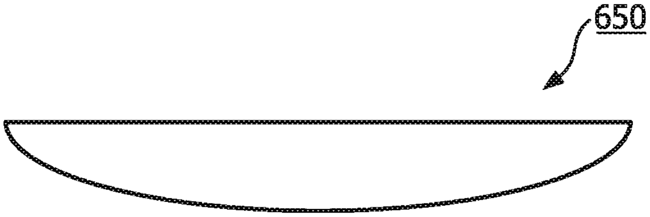
Figure 6C:
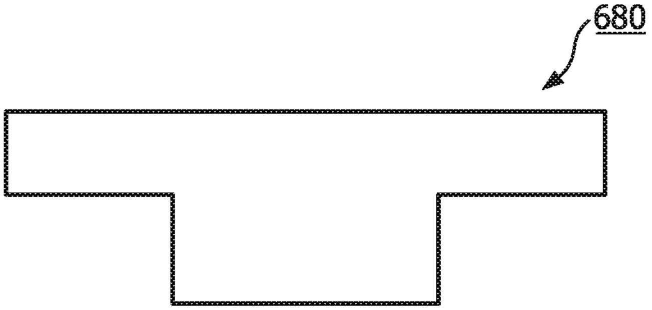

FIGS. 6A, 6B, and 6C are cross-sectional images of plates 600, 650, 680, respectively, according to aspects of the present disclosure. In some examples, the cross-sectional images correspond to the cross-section 6-6 in FIG. 3A, or similarly correspond to the cross-section 379 in FIG. 3B. FIGS. 6A, 6B, and 6C illustrates exemplary cross-sectional shapes of the plates 600, 650, 680. In various embodiments, the cross-section of the plates 600, 650, 680 may be solid. In other embodiments, the cross-section may include one or more openings. The plate 600 includes a rectangular cross-section, which advantageously provides a shape that can be easily manufactured. The plate 650 includes a semicircular or semi-elliptical shape, which may advantageously match a shape of the tip member 200 of the imaging device 110. The plate 680 includes a T-shape, which may advantageously add tensile/compressive strength and/or rigidity to inhibit deflection/bending of the plate.

Figure 7:
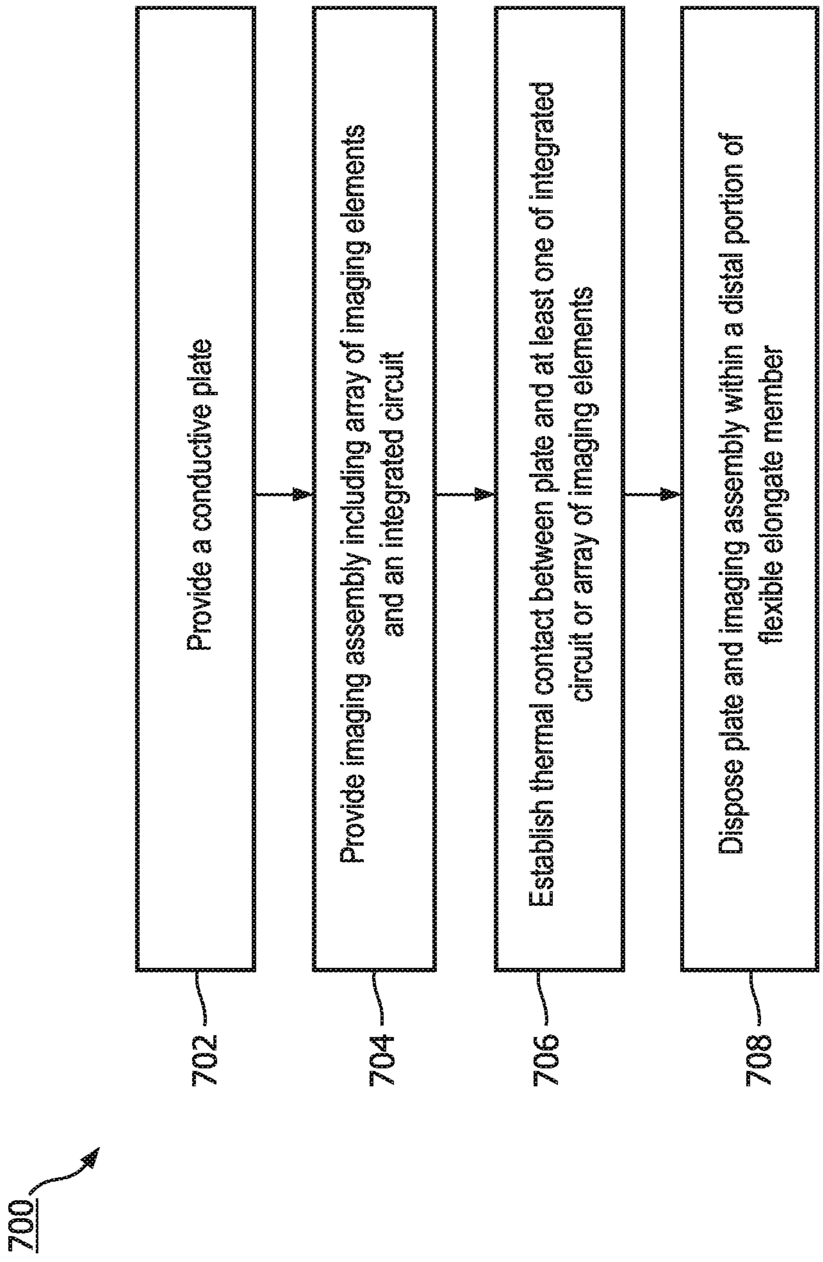
FIG. 7 is a flow diagram of a method of manufacturing an imaging device, according to aspects of the disclosure.

FIG. 7 provides a flow diagram illustrating a method 700 of manufacturing an imaging device, such as the device 110. It is understood that the steps of method 700 may be performed in a different order than shown in FIG. 7, additional steps can be provided before, during, and after the steps, and/or some of the steps described can be replaced or eliminated in other embodiments. The steps of the method 700 can be carried out by a manufacturer of the imaging device. In some examples, the device 110 may be used for intraluminal imaging, imaging fluid filled structures, or imaging within a body of a patient.

At step 702, the method 700 includes providing a conductive plate. At step 704, the method 700 includes providing an imaging assembly. The imaging assembly can include an array of imaging elements as well as an integrated circuit in communication with the array of imaging elements. In some embodiments, the imaging assembly may define a length of the imaging assembly. At step 706, the method 700 includes establishing thermal contact between the plate and one or more components of the imaging assembly, such as the array of imaging elements 302, the integrated circuit 304, the interconnect board 310, and/or the acoustic backing material 365. The plate can be adjacent to and extend at least a portion of the length of the imaging assembly. In some embodiments, step 706, establishing thermal contact can include bringing the components into direct or indirect contact or proximity such that heat energy can be transferred from one component to another. At step 708, the method 700 includes disposing the plate and the imaging assembly within a distal portion of a flexible elongate member. In some examples, disposing the plate and the imaging assembly may extend a length of the flexible elongate member. For example, step 708 can include mechanically and/or electrically attaching the plate and imaging assembly within the distal portion of the flexible elongate member. For example, the plate and the imaging assembly can be positioned within an imaging window or tip member that is coupled to the distal portion of the catheter body, such as the flexible elongate member.

In some embodiments, the plate is manufactured from a plate assembly. In that regard, the method 700 can include obtaining a plate assembly comprising a metal block coupled to a foil. The method 700 can include etching a plurality of plates in the metal, and not the foil, of the plate assembly. In this manner, the foil extending between the plates maintains the precise spacing between the plates. The method 700 can further include coupling one or more components of the imagining assembly on each respective plate. For example, at least a portion of the imaging assembly can include the acoustic backing material, the integrated circuit coupled to the acoustic backing material, and the array of imaging elements, e.g., transducer array, formed on the integrated circuit. These respective portions of the imaging assembly can be coupled to a distal portion of each plate. In that regard, step 706 can include coupling, such as by using an adhesive, a surface of the acoustic backing material of each imaging assembly to a respective plate of the plurality of plates. In that regard, pick and place processes can be used to precisely position the portions of the imaging assembly on respective plates of the plate assembly.

The portions of the imaging assembly connected to the plate can be referenced as a subassembly or plated imaging assembly in some embodiments. The method 700 can include singulating the subassemblies, such as the by etching, dicing, and/or otherwise cutting the foil of the plate assembly. This allows the subassemblies to be moved relative to one another. The method 700 can include adding additional components to each plated imaging assembly. For example, the method 700 can include establishing thermal contact between an interconnect board of the imaging assembly and the plate in some embodiments. For example, the interconnect board can be coupled to the acoustic backing material. Thus, heat from the interconnect board can be received by the plate via the acoustic backing material. The method 700 can also include mechanically and/or electrically coupling the integrated circuit and the interconnect board of the imaging assembly, such as with wire bonding 320. The method 700 can also include establishing electrical and/or mechanical contact between an electrical cable and the imaging assembly. The imaging assembly and plate can be attached to the distal portion of the flexible elongate member and extend a length of the flexible elongate member to form the imaging device.

The embodiment as described above pertains to ICE but could readily be translated to other invasive ultrasound imaging devices such as intravascular ultrasound devices and trans-oesophageal probes.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A device, comprising:

an intracardiac echocardiography (ICE) catheter comprising:

a catheter body comprising a distal portion sized and shaped for advancement through a blood vessel of a patient;

a tip member coupled to the distal portion of the catheter body such that the tip member is distinct from the catheter body, wherein the tip member comprises a smaller diameter distal region with a flat shape and a larger diameter proximal region with a rounded shape; and an imaging assembly comprising:

a first vertical stack comprising an array of imaging elements, an integrated circuit, and an acoustic backing material;

a second vertical stack comprising an interconnect board and a plurality of electronic components mounted on the interconnect board; and an electrical interconnection extending between the integrated circuit and the interconnect board, wherein the electrical interconnection is distinct from the first and second vertical stacks, wherein the first and second vertical stacks are longitudinally spaced from one another along a length of the ICE catheter, wherein the integrated circuit is below the array of imaging elements and above the acoustic backing material in the first vertical stack such that the first vertical stack is fitted inside the smaller diameter distal region and the array of imaging elements is proximate to the flat shape, and wherein the second vertical stack is fitted inside the larger diameter proximal region.

2. The device of claim 1, wherein a top surface of the integrated circuit is coupled to the array of imaging elements, and wherein a bottom surface of the integrated circuit is coupled to a top surface of the acoustic backing material.

3. The device of claim 1, wherein the imaging assembly comprises a thermally conductive plate having thermal contact with at least one of the integrated circuit or the array of imaging elements, and wherein the acoustic backing material is below the integrated circuit and above the thermally conductive plate in the first vertical stack.

4. The device of claim 3, wherein the thermally conductive plate comprises a metal alloy.

5. The device of claim 3, wherein the thermally conductive plate is radiopaque.

6. The device of claim 3, wherein a cross-section of the thermally conductive plate comprises a rectangular shape, a t-shape, or a semi-circular shape.

7. The device of claim 3, wherein a bottom surface of the acoustic backing material is coupled to a top surface of the thermally conductive plate.

8. The device of claim 3, wherein the acoustic backing material is thermally conductive such that the thermally conductive plate has thermal contact with at least one of the integrated circuit or the array of imaging elements via the acoustic backing material.

9. The device of claim 3, wherein a top surface of the thermally conductive plate comprises a first section and an opposite, second section, and wherein an entire length of the integrated circuit is disposed over the first section of the top surface of the thermally conductive plate.

10. The device of claim 3, wherein a length of the thermally conductive plate is oriented along a longitudinal axis of the ICE catheter.

11. The device of claim 3, wherein a bottom surface of the integrated circuit is disposed over a first section of a top surface of the thermally conductive plate, and wherein a bottom surface of the interconnect board is disposed over a second section of the top surface of the thermally conductive plate.

12. The device of claim 11, wherein:

the bottom surface of the integrated circuit is coupled to a top surface of the acoustic backing material, and the bottom surface of the interconnect board is coupled to the top surface of the acoustic backing material.

13. The device of claim 11, wherein a proximal end of the thermally conductive plate is aligned flush with a proximal end of the interconnect board.

14. The device of claim 11, wherein:

an entire length of the integrated circuit is disposed over a first section of the top surface of the thermally conductive plate, and an entire length of the interconnect board is disposed over a second section of the top surface of the thermally conductive plate.

15. The device of claim 11, wherein the thermally conductive plate extends from a proximal end of the interconnect board to a distal end of the integrated circuit.

16. The device of claim 11, wherein:

bottom surfaces of the integrated circuit, the interconnect board, and the thermally conductive plate are oriented in a same direction as one another, and top surfaces of the integrated circuit, the interconnect board, and the thermally conductive plate are oriented in a same direction as one another.

17. The device of claim 11, wherein:

bottom surfaces of the integrated circuit, the interconnect board, and the thermally conductive plate are parallel to one another, and top surfaces of the integrated circuit, the interconnect board, and the thermally conductive plate are parallel to one another.

18. The device of claim 3, wherein the thermally conductive plate is configured to draw and distribute heat generated by at least one of the array of imaging elements or the integrated circuit.

19. The device of claim 3, wherein the thermally conductive plate comprises a stiffness that is greater than a stiffness of the array of imaging elements and inhibits bending of the array of imaging elements.

20. The device of claim 1, wherein a distal end of the array of imaging elements, a distal end of the integrated circuit, and a distal end of the acoustic backing material are aligned flush with one another.

* * * * *